(12) United States Patent
Yin et al.

(10) Patent No.: US 10,702,885 B2
(45) Date of Patent: Jul. 7, 2020

(54) IMPLANT COATING AND DRYING DEVICE

(71) Applicant: Shenzhen ScienCare Medical Industries Co. Ltd., Shenzhen (CN)

(72) Inventors: Shugui Yin, Shenzhen (CN); Shiqiang Wang, Shenzhen (CN); Shaowei Jia, Shenzhen (CN); Tao Zhang, Shenzhen (CN); Qingzhe Liu, Shenzhen (CN)

(73) Assignee: Shenzhen ScienCare Medical Industries Co. Ltd., Shenzhen (CN)

( * ) Notice: Subject to any disclaimer, the term of this patent is extended or adjusted under 35 U.S.C. 154(b) by 54 days.

(21) Appl. No.: 16/137,532

(22) Filed: Sep. 20, 2018

(65) Prior Publication Data
US 2020/0061661 A1   Feb. 27, 2020

(30) Foreign Application Priority Data
Aug. 22, 2018  (CN) .......................... 2018 1 0962647

(51) Int. Cl.
| | | |
|---|---|---|
| *B05C 3/10* | (2006.01) | |
| *A61J 3/00* | (2006.01) | |
| *A61L 27/04* | (2006.01) | |
| *A61L 27/34* | (2006.01) | |

(Continued)

(52) U.S. Cl.
CPC ................ *B05C 3/10* (2013.01); *A23P 20/17* (2016.08); *A61J 3/005* (2013.01); *A61L 27/042* (2013.01); *A61L 27/34* (2013.01); *B05D 1/18* (2013.01)

(58) Field of Classification Search
CPC .......... A61J 3/005; B05C 3/10; A61K 9/2893; B05D 1/18
See application file for complete search history.

(56) References Cited

U.S. PATENT DOCUMENTS 3,046,143 A * 7/1962 Hamilton ................ A23P 20/11
                                                426/307
3,896,762 A * 7/1975 Banker ................... A61J 3/005
                                                118/30

(Continued)

FOREIGN PATENT DOCUMENTS

| CN | 1973840 | 6/2007 |
| CN | 102512399 | 6/2012 |

(Continued)

*Primary Examiner* — Karl Kurple
(74) *Attorney, Agent, or Firm* — JCIPRNET

(57) ABSTRACT

The present invention proposes an implant coating and drying device, including a chip sorter, a slide maker, a coating pool, a tablet pipe, a tablet conveying device, and a drying device. The chip sorter is connected to the slide maker, the shape of the coating pool is a circular arc. The coating pool is filled with coating solution. The inlet of the tablet pipe is connected with the slide maker, and the outlet of the tablet pipe is connected with the drying device, the tablet conveying device is used to deliver the implant tablet within the tablet pipe. The present invention proposes an implant coating and drying device, which has the advantages of simple structure and convenient operation, and avoids the defect of the prior art that the implant tablets adhere to each other, the coating is damaged, and the release degree of the implant tablet cannot be stabilized. The present invention proposes the implant coating and drying device is suitable for mass production.

7 Claims, 2 Drawing Sheets

(51) Int. Cl.
 *A23P 20/17* (2016.01)
 *B05D 1/18* (2006.01)

(56) References Cited

U.S. PATENT DOCUMENTS

| | | | | |
|---|---|---|---|---|
| 5,010,838 A | * | 4/1991 | Simelunas | A23G 3/26 118/19 |
| 5,942,034 A | * | 8/1999 | Brehant | A23G 3/24 118/20 |
| 2003/0118651 A1 | * | 6/2003 | Jampani | A61K 9/0024 424/473 |
| 2004/0234676 A1 | * | 11/2004 | Sheskey | A61K 9/2866 427/2.14 |
| 2010/0080897 A1 | * | 4/2010 | Fiesser | B05B 13/0257 427/212 |
| 2011/0091642 A1 | * | 4/2011 | Biel | B29D 11/00125 427/164 |
| 2012/0295848 A1 | * | 11/2012 | Yamamoto | A61K 9/1647 514/10.3 |
| 2015/0128854 A1 | * | 5/2015 | Ren | B05C 3/09 118/428 |
| 2018/0214957 A1 | * | 9/2018 | Enright | A23P 20/17 |

FOREIGN PATENT DOCUMENTS

| | | | | |
|---|---|---|---|---|
| CN | 108329125 | | 7/2018 | |
| CN | 209596217 | * | 11/2019 | A61J 3/00 |

\* cited by examiner

IMPLANT COATING AND DRYING DEVICE

CROSS-REFERENCE TO RELATED APPLICATION

This application claims the priority benefit of China application serial no. 201810962647.0, filed on Aug. 22, 2018. The entirety of the above-mentioned patent application is hereby incorporated by reference herein and made a part of this specification.

TECHNICAL FIELD

The present invention relates to a drug coating device, and more particularly, to an implant coating and a drying device.

BACKGROUND ART

In the study of sustained-release implants, the choice of biodegradable materials is essential. Polylactic acid is a kind of polymer with excellent biocompatibility and degradability, the final products of metabolism in the body are water and carbon dioxide, and the intermediate lactic acid is also a normal sugar metabolite in the body, does not accumulate in organs, and it is a medical excipient approved by the State Drug Administration. In order to ensure the compatibility of the drug, the implant coating is prepared by using the same or similar material as the sustained-release matrix, but the viscosity of the polylactic acid is very high, and the "wet" implants that have just been soaked in the coating solution adhere to each other, meantime destroy the yield of the coating, and it is not suitable for the coating operation. For example, Chinese patent CN200610152903.7 discloses a long-acting sustained-release preparation of naltrexone, which uses polylactic acid to coat naltrexone microspheres, and Chinese patent CN201110457641.6 discloses a long-acting naltrexone implant, the naltrexone microspheres after compression were also coated with DL-polylactic acid. However, as mentioned above, since the viscosity of polylactic acid is too high, the contact between the microspheres or the tablets after the coating, or the contact of the microspheres or tablets after the coating with the bottom surface of the tray during drying may cause the surface of the envelope film to adhere and rupture, affecting the integrity of the drug may cause the surface of the coating to adhere and rupture, affecting the integrity of the drug.

In the traditional process, in order to achieve the coloring, gastric dissolution, enteric dissolution, sustained release, controlled release and other effects of the tablets, the non-stick coating material is used, and the coating of the non-stick material can be coated in a spray-drying manner in the coating pool. However, the long-acting sustained-release drug is made of polylactic acid, which has a large viscosity. Many tablets are coated in one container at the same time, which inevitably causes the tablets to stick together.

At present, the research on the implant coating and the public literature technology are laboratory-level preparation processes, which cannot be mass-produced. Among them, many influencing factors and conditions obtained for screening are not applicable in large-scale production, this is because the active ingredients of the microspheres are different, the way of adding the internal phase emulsion to the external phase solution is different, the composition of the solution is different, and the specific excipient ingredients used are different, which will lead to the unpredictable changes of the preparation process conditions. Therefore, it is necessary to re-examine the study in order to obtain the ideal sustained release implant with a sustained release effect and a therapeutic effect.

Chinese patent (a coating device for slow release fertilizer: CN201810333180.3) discloses a coating device for slow release fertilizer comprises a supporting device and a coating mechanism mounted on the supporting device; the coating mechanism comprises a coating cylinder and a feeding funnel fixed at an upper end of the coating cylinder; a screen is fixed on a circumferential inner surface of the coating cylinder, and a discharge slot is provided at a joint between the screen and the side wall of the coating cylinder; the side wall surface of the coating cylinder is provided with a circular hole which cooperates with the spray pipe, and the spray pipe penetrates the side wall of the coating cylinder through the circular hole; and a heating tube is fixed to an inner surface of the wall of the coating cylinder. Although the coating device of the patent has a simple structure, the patent uses a spray pipe for coating, and it is impossible to uniformly spray the viscous coating solution, which may cause adhesion of the implant tablet to the wall of the coating cylinder, and the coating is incomplete and uneven, and the thickness of the slow-release fertilizer after the coating is not uniform, resulting in uneven release performance, which increases the cost.

SUMMARY OF THE INVENTION

In order to solve the problems existing in the prior art, the present invention proposes an implant coating and drying device, which has a simple structure and convenient operation, and avoids the drawback of the prior art that the coating preparation of the implants can only be performed in the laboratory and cannot be mass produced.

To solve the above technical problems, the present invention provides an implant coating and drying device, comprising a chip sorter, a slide maker, a coating pool, a tablet pipe, a tablet conveying device, and a drying device. The chip sorter is connected to the slide maker, a shape of the coating pool is a circular are, and the coating pool is filled with coating solution. An inlet of the tablet pipe is connected with the slide maker, and an outlet of the tablet pipe is connected with the drying device, wherein the tablet conveying device is used to deliver the implant tablet within the tablet pipe.

Preferably, the tablet pipe comprises a first tablet pipe, a second tablet pipe, a third tablet pipe, and a fourth tablet pipe, wherein the first tablet pipe, the second tablet pipe, the third tablet pipe, and the fourth tablet pipe are all stainless-steel tubes. The first tablet pipe, the second tablet pipe, the third tablet pipe, and the fourth tablet pipe are disposed as an integral structure, wherein the first tablet pipe, the second tablet pipe, the third tablet pipe, and the fourth tablet pipe are sequentially connected, the first tablet pipe is connected to the slide maker, the third tablet pipe is disposed in a slanted orientation, an inclination angle of the third tablet pipe is 5-20° in relative to the plane of the ground, the fourth tablet pipe is vertically disposed, and an outlet of the fourth tablet pipe extends into the drying device.

Preferably, the first tablet pipe proposed by the present invention is disposed in parallel. The inlet of the first tablet pipe is connected to the slide maker. The outlet of the first tablet pipe is connected to the inlet of the second tablet pipe. The second tablet pipe has a circular arc shape and is laid in the coating pool. The third tablet pipe is disposed in a slanted orientation, and the fourth tablet pipe is vertically disposed.

Preferably, a bottom end of the second tablet pipe is attached to an inside of the coating pool, and the second tablet pipe is immersed in the coating solution.

Preferably, the second tablet pipe is provided with a mesh, wherein a mesh density is at least 100/30 cm, and a diameter of the mesh is 2 mm.

Preferably, a diameter of the second tablet pipe gradually decreases from an inlet of the second tablet pipe to an outlet of the second tablet pipe, and a diameter of the inlet of the second tablet pipe is 0.5-1.5 mm larger than a diameter of the outlet of the second tablet pipe, the diameter of the outlet of the second tablet pipe is 1.5-2 mm larger than a diameter of the implant tablet.

Preferably, the diameter of the inlet of the second tablet pipe is 0.9 mm larger than the diameter of the outlet, the diameter of the outlet of the second tablet pipe is 1.5 mm larger than the diameter of the implant tablet.

Preferably, the second tablet pipe is provided with a first push rod track, and the third tablet pipe is provided with a second push rod track; wherein the tablet conveying device comprises a first driving device, a rotational push rod, a second driving device and a translational push rod. The shape of the coating pool is a circular arc, and the first driving device is disposed at the center of the circular arc. The second driving device is disposed at an upper end of the third tablet pipe. One end of the rotational push rod is connected to the first driving device, and the other end of the rotational push rod extends into the second tablet pipe through the first push rod track. One end of the translational push rod is connected to the second driving device, and the other end of the translational push rod extends into the third tablet pipe through the second push rod track.

Preferably, the rotational push rod and the translational push rod are made of steel with TEFLON (polytetrafluoroethylene) on surfaces of the rotational push rod and the translational push rod.

The coating solution is a polylactic acid solution, and a concentration of the polylactic acid solution is 5-9 wt %.

Preferably, the drying device comprises a blower, an air duct, a collecting device, an automatic control system, a push rod, and a third driving device, wherein a lower end of the air duct is connected to the blower through a blower pipe, and the blower supplies wind power to the air duct through the blower pipe. A screen is arranged at a joint between the air duct and the blower pipe, the screen is disposed in a slanted orientation, and the inclination angle of the screen is 10°. The collecting device is disposed at a lower end of the screen, wherein the third driving device is connected to the push rod for controlling the push rod to push the implant tablet on the screen into the collecting device. The air duct is a double-layered sleeve structure, and a diameter of an outer layer of the air duct is 10 mm larger than a diameter of an inner layer of the air duct, forming a gap between an outer cylinder wall of the air duct and an inner cylinder wall of the air duct. The inner cylinder wall of the air duct is evenly covered with a plurality of first holes, a spacing between each of the first holes is 2 mm, and a diameter of the first hole is 1 mm. A top of the air duct is provided with an opening for loading the implant tablet, wherein the automatic control system is used to control a speed of the blower, and thus a suspension time of the implant tablet in the air duct can be controlled.

Preferably, the screen has a plurality of second holes uniformly distributed, a spacing between each of the second holes is 2 mm, and a diameter of the second hole is 3 mm.

Comparing to the prior art, the beneficial effects produced by the present invention are:

(1) The special coating device of the present invention enables the polylactic acid with higher viscosity to be uniformly wrapped on the surface of implant tablets, thereby effectively avoiding the problem of incomplete coating caused by adhesion between each other, and overcoming the problem that the coating is incomplete when the polylactic acid is used as the coating solution in the prior art.

(2) The diameter of the tablet pipe (especially the second tablet pipe) and the implant tablet proposed by the present invention is very important, and the diameter of the outlet of the second tablet pipe is 0.5-1.5 mm larger than the diameter of the tablet, which can effectively ensure the consistency of the thickness of the implant tablet and avoid the problem of uneven coating quality.

(3) The present invention proposes an implant coating and drying device, which has the advantages of simple structure and convenient operation, and avoids the defect of the prior art that the implant tablets adhere to each other, the coating is damaged, and the release degree of the implant tablet cannot be stabilized. The present invention proposes the implant coating and drying device is suitable for mass production.

(4) The diameter of the second tablet pipe of the present invention gradually decreases from the inlet to the outlet, which ensure the integrity of the coating, and make the thickness of the implant tablet to be uniform.

(5) The coating solution provided in the present invention is a high-viscosity material which may lose its viscosity after being dried in the air. Therefore, multiple implant tablets cannot be coated together by using a conventional boiling dryer. The drying device provided by the present invention can realize a single implant tablet coating to prevent blocking, control the temperature and time of the coating process, and ensure that the coating difference of each implant tablet is small, and the difference of the release of each implant tablet is less than 3%.

(6) The automatic control system in the drying device proposed by the present invention can control the time for coating and drying of the implant tablet, and when the drying time is 30 seconds, the effect is best, which can prevent the coating formation from being too fast or too slow. When the drying speed is too fast, the implant tablet is likely to be formed with bubbles; and when the drying speed is too slow, the production efficiency is affected.

(7) The coating integrity, uniformity, thickness, and coating speed of the coating and drying device proposed by the present invention are related to the diameter of the second tablet pipe, the concentration of the coating solution, and the coating time; they are interactive to each other so as to avoid the coating speed being too slow, which may cause the coating solution penetrating inward and destroying the microspheres and the skeleton.

(8) The coating temperature and time of the present invention have a great influence on the quality of the coating. Due to the large viscosity of the PLA, it is difficult to form a uniform coating on the surface of the implants. Strictly controlling the temperature and time of the coating process helps to form thin coating, and the integrity of the coating in the present invention is more than 99%.

(9) The first driving device and the rotational push rod proposed by the present invention can control the coating time of each implant tablet in the coating solution, thereby controlling the coating thickness of each tablet. When the time for the implant tablet to pass through the coating solution is 30 seconds, the coating thickness is appropriate and the integrity is good.

Figure 1:
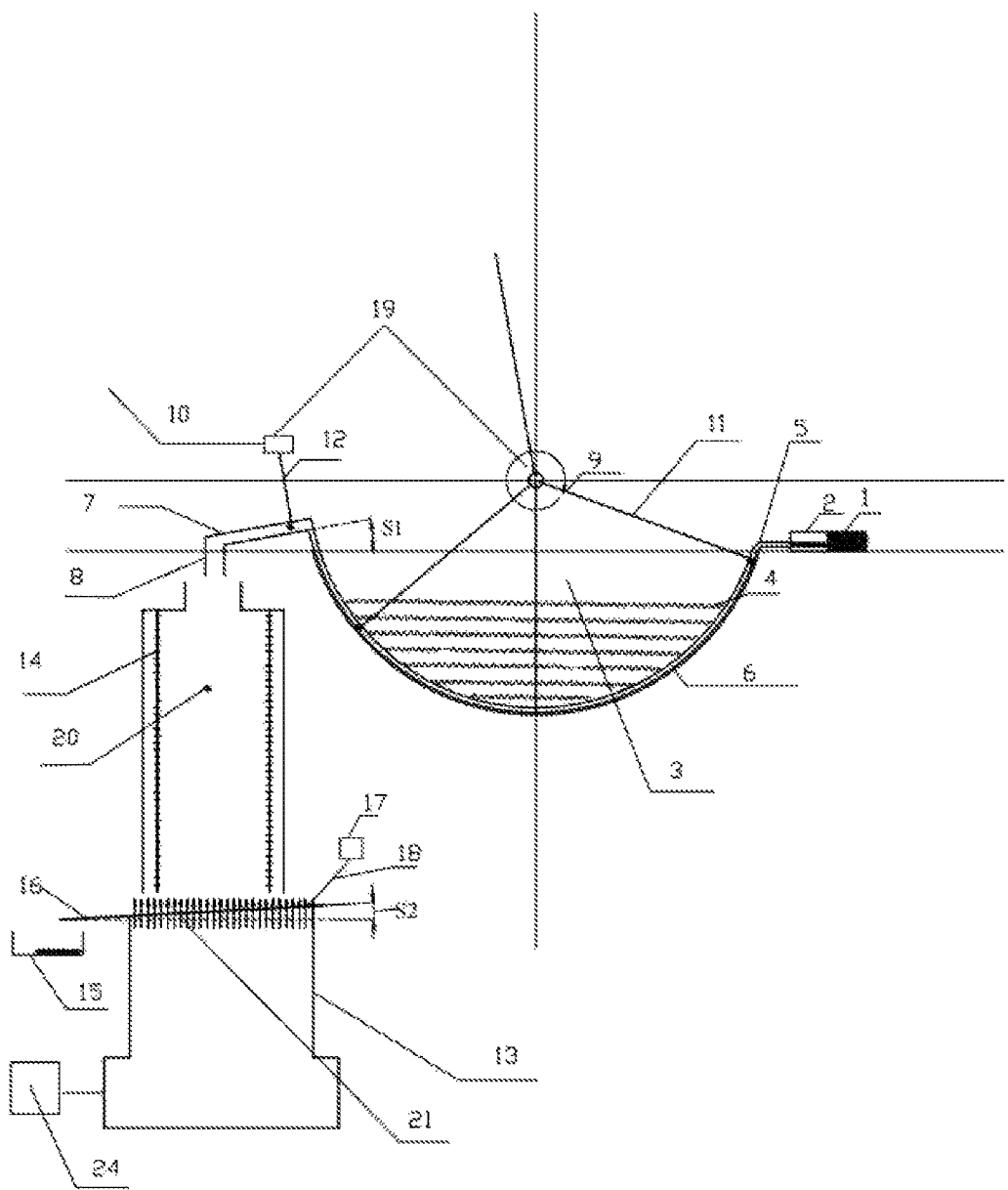
FIG. 1 is a schematic structural view of an implant coating and drying device, according to the present invention.

The specific meanings of the marks in the drawings are as follows:

1: chip sorter; 2: slide maker; 3: coating pool; 4: coating solution; 5: first tablet pipe; 6: second tablet pipe; 7: third tablet pipe; 8: fourth tablet pipe; 9: first driving device; 10: second driving device; 11: rotational push rod; 12: translational push rod; 13: blower; 14: air duct; 15: collection device; 16: screen; 17: third driving device; 18: push rod; 19: tablet conveying device; 20: implant tablet; 21: blower pipe; 22: first push rod track; 23: second push rod track; 24: automatic control system; S1, S2: inclination angle.

DETAILED DESCRIPTION OF THE PREFERRED EMBODIMENT

The specific embodiments of the present invention will be described in detail below with reference to the attached drawing.

FIG. 1 is a schematic structural view of an implant coating and drying device of the present invention.

Figure 2:
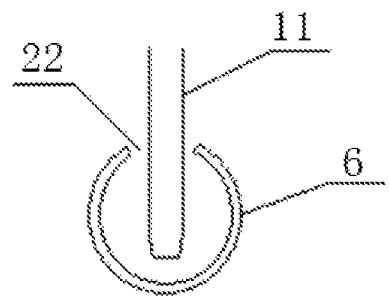
FIG. 2 is a cross-sectional view of the second tablet pipe provided by the present invention.

FIG. 2 is a cross-sectional view of the second tablet pipe provided by the present invention.

Figure 3:
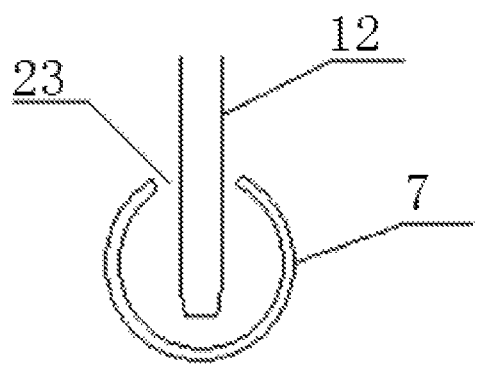
FIG. 3 is a cross-sectional view of the third tablet pipe provided by the present invention.

FIG. 3 is a cross-sectional view of the third tablet pipe provided by the present invention.

Referring to FIG. 1 to FIG. 3, an implant coating and drying device comprises: a chip sorter 1, a slide maker 2, a coating pool 3, a tablet pipe, a tablet conveying device 19, and a drying device; the chip sorter 1 is connected to the slide maker 2, the shape of the coating pool 3 is a circular arc; the coating pool 3 is filled with coating solution; the inlet of the tablet pipe is connected with the slide maker 2, and the outlet of the tablet pipe is connected with the drying device, the tablet conveying device 19 is used to deliver the implant tablet 20 within the tablet pipe.

The implant coating and drying device proposed by the present invention further comprises a micro motor and an automatic control device, the slide maker 2 is electrically connected with the micro motor, the slide maker 2 is provided with a pusher, the pusher is electrically connected with the automatic control device, and the automatic control device is used to control the micro-motor drive pusher to push the implant tablet 20 movement.

The tablet pipe proposed by the present invention is divided into four segments; respectively, a first tablet pipe 5, a second tablet pipe 6, a third tablet pipe 7, and a fourth tablet pipe 8; the first tablet pipe 5, the second tablet pipe 6, the third tablet pipe 7, and the fourth tablet pipe 8 are all stainless-steel tubes, the first tablet pipe 5, the second tablet pipe 6, the third tablet pipe 7, and the fourth tablet pipe 8 are disposed as an integral structure, and the first tablet pipe 5, the second tablet pipe 6, the third tablet pipe 7, and the fourth tablet pipe 8 are sequentially connected.

The first tablet pipe 5 proposed by the present invention is disposed in parallel, the inlet of the first tablet pipe 5 is connected to the slide maker 2, the outlet of the first tablet pipe 5 is connected to the inlet of the second tablet pipe 6; the second tablet pipe 6 has a circular arc shape and is laid in the coating pool 3, the third tablet pipe 7 is disposed in a slanted orientation, and the fourth tablet pipe 8 is vertically disposed.

The first tablet pipe 5 proposed by the present invention is connected to the slide maker 2, the third tablet pipe 7 is disposed in a slanted orientation, with an the inclination angle S1 of the third tablet pipe is 5-20°, the fourth tablet pipe 8 is vertically disposed, and the outlet of the fourth tablet pipe 8 extends into the drying device. The bottom end of the second tablet pipe 6 proposed by the present invention is attached to the inside of the coating pool 3, and the second tablet pipe 6 is immersed in the coating solution.

The second tablet pipe 6 proposed by the present invention has a length of 30 cm, and the second tablet pipe 6 is provided with compact mesh, and the mesh density is at least 100/30 cm; the diameter of the mesh is 2 mm.

The diameter of the second tablet pipe 6 gradually decreases from an inlet of the second tablet pipe to an outlet of the second tablet pipe, and the diameter of the outlet of the second tablet pipe 6 is 1.5-2 mm larger than the diameter of the implant tablet 20. When the diameter of the inlet of the second tablet pipe 6 is 0.9 mm larger than the diameter at the outlet and the diameter of the outlet of the second tablet pipe 6 is 1.5 mm larger than the diameter of the implant tablet 20, the thickness and integrity of the coating are better.

The second tablet pipe 6 and the third tablet pipe 7 proposed by the present invention are respectively provided with a first push rod track 22 and a second push rod track 23; the first push rod track 22 is matched with the rotational push rod 11 and the first push rod rail is an opening with a width of 2 mm, and the diameter of the rotational push rod 11 is 1.5 mm. The second push rod is matched with the translational push rod 12 and the second push rod track 23 is an opening with a width of 2 mm, and the diameter of the translational push rod 12 is 1.5 mm.

The tablet conveying device 19 proposed by the present invention comprises a first driving device 9, a rotational push rod 11, a second driving device 10 and a translational push rod 12, the first driving device 9 is disposed at a circle center of the coating pool 3; and the second driving device 10 is disposed at an upper end of the third tablet pipe 7.

One end of the rotational push rod 11 is connected to the first driving device 9, and the other end of the rotational push rod 11 extends into the second tablet pipe 6 through the first push rod rail; one end of the translational push rod 12 is connected to the second driving device 10, and the other end of the translational push rod 12 extends into the third tablet pipe 7 through the second push rod track 23. The rotational push rod 11 and the translational push rod 12 are made of steel with TEFLON on the surface, wherein TEFLON is actually made of polytetrafluoroethylene (PTFE).

The coating solution is a polylactic acid solution, and the concentration of the polylactic acid solution is 5-9 wt %.

The drying device proposed by the present invention comprises a blower 13, an air duct 14, a collecting device 15, an automatic control system 24, a push rod 18, and a third driving device 17, the lower end of the air duct 14 is connected to the blower 13 through a blower pipe 21, a screen 16 is arranged at a joint between the air duct 14 and the blower pipe 21; the screen 16 is disposed in a slanted orientation, and the inclination angle S2 of the screen is 10°; the collecting device 15 is disposed at a lower end of the screen 16.

The third driving device 17 is connected to the push rod 18 for controlling the push rod 18 to push the implant tablet 20 on the screen 16 into the collecting device 15.

The air duct 14 is a double-layered sleeve structure, and a diameter of the outer layer of the air duct is 10 mm larger than an diameter of an inner layer, forming a gap between an outer cylinder wall of the air duct and an inner cylinder wall of the air duct; the inner cylinder wall of the air duct is evenly covered with a plurality of first holes; the spacing between each of the first holes is 2 mm, and the diameter of the first hole is 1 mm; and the top of the air duct 14 is provided with an opening for loading the implant tablet 20. The automatic control system 24 is used to control the speed of the blower 13, thereby controlling the suspension time of the implant tablet 20 in the air duct 14, and the suspension time is 30 seconds.

The screen 16 has a plurality of second holes uniformly distributed, and the spacing between each of the second holes is 2 mm, the diameter of the second hole is 3 mm.

Treatment Process of Implant Coating and Drying Device.

The implant tablet 20 is discharged from the chip sorter 1 into the slide maker 2, and the slide maker 2 pushes the implant tablet 20 into the tablet pipe, and the implant tablet 20 enters the second tablet pipe 6 along the first tablet pipe 5, controlling the time of the implant tablet 20 in the second tablet pipe 6 to be 15 seconds to 50 seconds by a first driving device 9 and a rotational push rod 11, preferably 30 seconds. The coating process temperature is controlled between 33-40° C., preferably 37° C. After the coating in the second tablet conduit 6 is completed, the coated implant tablet 20 enters the third tablet pipe 7, and the implant tablet 20 is pushed into the drying device by the second driving device 10 and the translational push rod 12 to dry. The drying device uses the lift of the airflow to "lift" the implant tablet 20 falling from the fourth tablet pipe, and the implant tablet 20 suspends in the airflow, and the high-viscosity emulsion coated on the surface of the implant tablet 20 is volatilized and dried to form a coat that is no longer sticky; the automatic control system 24 controls the speed of the blower so that the implant tablet 20 is suspended and dried in the wind tunnel for 30 seconds; after the implant tablet 20 is suspended for 30 seconds, the automatic control system 24 controls the speed of the blower 13 to decrease, so that the buoyancy of the wind is reduced, and the implant tablet 20 falls into the screen 16; at this time, the push rod 18 is driven by the third driving device 17 to push the implant tablet 20 into the collecting device 15 and collect it. The suspension drying temperature proposed by the present invention is 18 to 24° C., and preferably, the drying temperature is 20° C.

Example 1: Coating and Drying Process of Naltrexone Implants (1) Dissolving polylactic acid with a molecular weight of 60,000 in dichloromethane to form coating solution 4, and the concentration of the coating solution is 6%, putting the coating solution into the coating pool 3.

(2) Pushing the naltrexone implant tablet 20 into the first tablet pipe 5 by the slide maker 2, then entering the second tablet pipe 6, and pushing the implants tablet from the inlet of the second tablet pipe 6 to the outlet of the second tablet pipe 6 by the first driving device 9 and rotational push rod 11 to coat the tablets; and the coating time is 30 seconds, and the coating temperature is 37° C.

(3) The coated naltrexone implant tablet 20 is pushed into the third tablet pipe 7 by the rotational push rod, and then the naltrexone implant tablet 20 is pushed from the fourth tablet pipe 8 into the drying device through the translational push rod 12 to dry at 20° C. for 30 seconds.

Wherein, the mesh density on the second tablet pipe 6 is 100/30 cm; the diameter of the mesh is 2 mm, the diameter of the inlet of the second tablet pipe 6 is 0.9 mm larger than the diameter at the outlet, the diameter of the outlet of the second tablet pipe 6 is 1.5 mm larger than the diameter of the naltrexone implant tablet 20.

The coating thickness of the naltrexone implant tablet 20 obtained by the above coating process was determined to be 0.002-0.003 mm, and the coating integrity was 100%.

The detailed descriptions of the foregoing are merely illustrative of the possible embodiments of the present invention, and are not intended to limit the scope of the present invention, which is within the knowledge of one of ordinary skill in the art. Various changes made without departing from the spirit of the invention are within the scope of the invention.

The invention claimed is:

1. An implant coating and drying device comprising:
   a chip sorter;
   a slide maker;
   a coating pool;
   a tablet pipe;
   a tablet conveying device; and
   a drying device,
   wherein the chip sorter is connected to the slide maker, a shape of the coating pool is a circular arc,
   wherein the coating pool is filled with a coating solution,
   wherein an inlet of the tablet pipe is connected with the slide maker, and an outlet of the tablet pipe is connected with the drying device,
   wherein the tablet conveying device is used to deliver an implant tablet within the tablet pipe,
   the tablet pipe comprising:
      a first tablet pipe;
      a second tablet pipe;
      a third tablet pipe; and
      a fourth tablet pipe,
      wherein the first tablet pipe, the second tablet pipe, the third tablet pipe, and the fourth tablet pipe are all stainless steel tubes,
      wherein the first tablet pipe, the second tablet pipe, the third tablet pipe, and the fourth tablet pipe are disposed as an integral structure,
      wherein the first tablet pipe, the second tablet pipe, the third tablet pipe, and the fourth tablet pipe are sequentially connected,
      wherein the first tablet pipe is connected to the slide maker, the third tablet pipe is disposed in a slanted orientation, an inclination angle of the third tablet pipe is 5-20° relative to a ground plane, the fourth tablet pipe is vertically disposed, and an outlet of the fourth tablet pipe extends into the drying device.

2. The implant coating and drying device according to claim 1, wherein a bottom end of the second tablet pipe is attached to an inside of the coating pool, and the second tablet pipe is immersed in the coating solution.

3. The implant coating and drying device according to claim 1, wherein a diameter of the second tablet pipe gradually decreases from an inlet of the second tablet pipe to an outlet of the second tablet pipe, and a diameter of the outlet of the second tablet pipe is 1.5-2 mm larger than a diameter of the implant tablet.

4. The implant coating and drying device according to claim 1, wherein the second tablet pipe is provided with a first push rod track, and the third tablet pipe is provided with a second push rod rail, wherein the tablet conveying device comprises a first driving device, a rotational push rod, a second driving device and a translational push rod, wherein the first driving device is disposed at the center of the circular arc of the coating pool, and the second driving device is disposed at an upper end of the third tablet pipe, wherein one end of the rotational push rod is connected to the first driving device, and the other end of the rotational push rod extends into the second tablet pipe through the first push rod track, wherein one end of the translational push rod is connected to the second driving device, and the other end of the translational push rod extends into the third tablet pipe through the second push rod track.

5. The implant coating and drying device according to claim 4, wherein the rotational push rod and the translational push rod are made of steel with polytetrafluoroethylene on surfaces of the rotational push rod and the translational push rod.

6. The implant coating and drying device according to claim 1, wherein the drying device comprises:
a blower;
an air duct;
a collecting device;
an automatic control system;
a push rod; and
a third driving device,
wherein a lower end of the air duct is connected to the blower through a blower pipe, and the blower supplies wind power to the air duct through the blower pipe, wherein a screen is arranged at a joint between the air duct and the blower pipe, wherein the screen is disposed in a slanted orientation, and an inclination angle of the screen is 10° relative to the ground plane, wherein the collecting device is disposed at a lower end of the screen, wherein the third driving device is connected to the push rod for controlling the push rod to push the implant tablet on the screen into the collecting device, wherein the air duct is a double-layered sleeve structure, and a diameter of an outer layer of the air duct is 10 mm larger than a diameter of an inner layer of the air duct, forming a gap between an outer cylinder wall of the air duct and an inner cylinder wall of the air duct, wherein the inner cylinder wall of the air duct is evenly covered with a plurality of first holes, a spacing between each of the first holes is 2 mm, and a diameter of the first hole is 1 mm, wherein a top of the air duct is provided with an opening for loading the implant tablet, wherein the automatic control system is used to control a speed of the blower, thereby controlling a suspension time of the implant tablet in the air duct.

7. The implant coating and drying device according to claim 6, wherein the screen has a plurality of second holes uniformly distributed, and a spacing between each of the second holes is 2 mm, and a diameter of the second hole is 3 mm.

* * * * *